US008852159B2

(12) United States Patent
Neale et al.

(10) Patent No.: US 8,852,159 B2
(45) Date of Patent: Oct. 7, 2014

(54) INJECTION DEVICE PREVENTING THE RETURN OF THE PISTON WHEN THE SAFETY SYSTEM IS DEPLOYED

(75) Inventors: Kevin David Neale, Swindon (GB); Eric Dominicy-Lenoble, Revel (FR)

(73) Assignee: Becton Dickinson France S.A.S., Le Pont de Claix (FR)

( * ) Notice: Subject to any disclaimer, the term of this patent is extended or adjusted under 35 U.S.C. 154(b) by 1126 days.

(21) Appl. No.: 12/442,174

(22) PCT Filed: Sep. 19, 2007
(Under 37 CFR 1.47)

(86) PCT No.: PCT/IB2007/003782
§ 371 (c)(1),
(2), (4) Date: Apr. 15, 2010

(87) PCT Pub. No.: WO2008/035226
PCT Pub. Date: Mar. 27, 2008

(65) Prior Publication Data
US 2011/0230832 A1    Sep. 22, 2011

(30) Foreign Application Priority Data
Sep. 20, 2006  (FR) ..................................... 06 08229

(51) Int. Cl.
*A61M 5/32* (2006.01)
*A61M 5/315* (2006.01)

(52) U.S. Cl.
CPC ....... *A61M 5/326* (2013.01); *A61M 2005/3264* (2013.01); *A61M 2005/3261* (2013.01); *A61M 5/31511* (2013.01)
USPC .......................................... 604/198; 604/218

(58) Field of Classification Search
USPC .......... 604/110, 187, 192, 198, 218, 228, 263
See application file for complete search history.

(56) References Cited

U.S. PATENT DOCUMENTS 4,915,692 A    4/1990  Verlier
5,085,638 A *  2/1992  Farbstein et al. ............. 604/110
(Continued)

FOREIGN PATENT DOCUMENTS

FR    2706776 A1    12/1994
FR    2711532 A1     5/1995
(Continued)

*Primary Examiner* — Nicholas Lucchesi
*Assistant Examiner* — Leah Stohr
(74) *Attorney, Agent, or Firm* — Hoffmann & Baron, LLP (57) ABSTRACT

The present invention relates to an injection device (1) comprising:—a body (3) designed to receive a product to be injected, furnished at its distal end with an injection needle (7) and receiving a piston (5) capable of being moved between a storage position and an end-of-injection position under the effect of a distal pressure exerted on a piston rod (8) to the distal end of which it is attached,—means of protecting the injection needle (7) capable of adopting an initial position, during which the injection needle (7) is uncovered, and a final position, in which the said injection needle (7) is covered,—biasing means (26) aiming at moving the said covering element (6) from its initial position to its final position,—immobilization means (16, 31) aiming at keeping the said covering element (6) in its initial position, the said injection device (1) being characterized in that:—the said piston rod (8) comprises at least a first portion (9) and at least one second portion (10) coupled to the said piston (8), the said first and second portions (9, 10) being operatively coupled together and selectively movable together in the distal direction, at least one of said first portion (9) and said second portion (10) being movable in the proximal direction separate from said other one of said first portion (9) and said second portion (10).

29 Claims, 8 Drawing Sheets

(56) References Cited

U.S. PATENT DOCUMENTS

| | | | |
|---|---|---|---|
| 5,163,918 A * | 11/1992 | Righi et al. | 604/198 |
| 6,966,898 B1 | 11/2005 | Pouget et al. | |
| 7,118,552 B2 * | 10/2006 | Shaw et al. | 604/110 |
| 7,682,344 B2 | 3/2010 | Barrelle | |
| 2004/0158205 A1 | 8/2004 | Savage | |
| 2005/0080383 A1* | 4/2005 | Woehr | 604/198 |
| 2005/0148943 A1 | 7/2005 | Chevalier | |
| 2007/0179441 A1* | 8/2007 | Chevallier | 604/110 |
| 2008/0208140 A1* | 8/2008 | Barrelle | 604/198 |

FOREIGN PATENT DOCUMENTS

| | | |
|---|---|---|
| FR | 2799976 A1 | 4/2001 |
| FR | 2861310 A1 | 4/2005 |
| FR | 2861598 A1 | 5/2005 |
| WO | 0204049 A1 | 1/2002 |
| WO | 03068298 A1 | 8/2003 |
| WO | 2004033006 A2 | 4/2004 |
| WO | 2005030302 A1 | 4/2005 |
| WO | 2008035226 A3 | 3/2008 |

* cited by examiner

INJECTION DEVICE PREVENTING THE RETURN OF THE PISTON WHEN THE SAFETY SYSTEM IS DEPLOYED

The present invention relates to a product injection device, particularly for medical use, such as syringes, particularly furnished with a safety system aimed at protecting the injection needle after use.

In this application, the distal end of a component or of a device means the end furthest away from the hand of the user and the proximal end means the end closest to the hand of the user. Similarly, in this application, the terms "in the distal direction" and "distally" mean in the direction of the injection, and the terms "in the proximal direction" and "proximally" mean in the direction opposite to the direction of injection.

Product injection devices, such as syringes, are well known. These injection devices are usually furnished at their distal end with an injection needle that is designed to be inserted into the skin of a patient, and through which the product to be injected passes to the injection site. Normally, these syringes are furnished with a piston rod whose distal end comprises a piston which, during the injection phase and under the action of a distal pressure exerted by the user on the piston rod, pushes the product through the injection needle.

One of the constant problems presented by the injection devices is the risk of accidental pricks likely to occur after the injection.

In order to minimize these risks, it is known practice to furnish the syringes with means of protecting the needle after injection: these protection means may for example be in the form of a sleeve sliding relative to the syringe and required to cover the needle after the injection and the withdrawal of the needle from the injection site.

Certain of these protection means must be activated manually, the sleeve having to be moved manually by the end-user to cover the needle. Consequently, these protection means are not very reliable and not very practical to use. To remedy these disadvantages, injection devices have been designed with protection means that are automatically activated, for example by the movement of the piston rod which, when it reaches a predetermined position, releases the sleeve then deployed without additional manual intervention, by elastic means, for example a spring forcing its distal movement at the end of injection.

However, it happens that the automatic protection means are activated while the needle is still in the skin of the patient. In such a case, the sleeve begins to deploy and is then stopped by the skin of the patient against which it is pressed by the spring. The spring can therefore not deploy further in the distal direction and tends to deploy in the proximal direction, which causes the piston rod, and hence the piston, to rise again in the proximal direction into the body of the injection device. In other cases as described hereinafter, the piston rod is caused to rise again by the means for activating the protection means returning elastically to their initial position.

The user may then be confronted with a problem of reabsorption of the injected product due to the return movement of the piston rod, and hence of the piston, in the proximal direction. This return movement is usually limited in distance: however, it is sufficient to cause a portion of the product previously injected into the body of the patient to return into the body of the syringe, thereby causing an incorrect dosage of the injected product. The recommended dose of product is not injected in its totality and serious consequences for the patient may result therefrom.

Thus, there is the need for an injection device comprising automatic means of protecting the needle making it possible to prevent the phenomenon of the return of the piston in the proximal direction after injection, in particular when the injection needle remains at least for a moment in the skin of the patient after the end of the injection and when the automatic protection means are activated before it is withdrawn.

Publication WO 03/068298 A1 describes an injection device provided with automatic protection means activated by the piston rod when the latter arrives at the end of travel towards the end of the dose. The protection means comprise a covering element held in a sheath by elastically flexible lateral lugs designed to be deflected by the head of the piston rod when the latter arrives at the end of travel. The spring provided for deploying the covering element is placed between the sheath and the covering element itself. Thus, if, at the end of injection, while the needle is still in the injection site, the user stops pressing on the piston rod, the spring will only have the effect of pressing the covering element towards the skin of the patient without causing the piston rod to rise again. Nevertheless, this injection device has the major disadvantage of not allowing the moment when the protection means are activated to be controlled. It is therefore difficult, even impossible, to perform the injection of the end of the dose followed by the activation of the protection means. Also, in the majority of cases of use, the covering element is released and pressed against the skin when the whole dose of product has not yet been injected. Furthermore, the sheath of this injection device comprises elastically flexible intermediate lugs placed between the lateral lugs and the head of the piston rod. When the automatic protection means are triggered, if the user relaxes the pressure of the piston rod, the intermediate lugs return to their undeflected position causing the piston to rise again, hence a risk of reabsorption of the previously injected product.

There is therefore also the need for such an injection device making it possible to trigger the activation of the protection means at the moment desired by the user and to ensure that the end of the dose of product is injected without reabsorption.

Specifically, one of the problems encountered with the automatic protection means is the risk of activating them prematurely or inadvertently, during their use, even during the manufacture and/or assembly of the injection devices. Another associated risk is that of, after activation of the protection means, no longer being able to inject the end of the dose. Also, to alleviate these problems, the injection devices must be manufactured with extremely tight production tolerances aimed at the end of the dose coinciding with the activation of the activation means. These production tolerances are difficult to guarantee; the industrial processes for manufacturing the injection devices are thereby complicated and slowed and the injection device is more costly.

Publication WO 2005/030301 A1 describes an injection device provided with automatic protection means activated by the piston rod when the latter arrives at the end of travel towards the end of the dose. The automatic protection means comprise a covering element designed to be deployed by a spring. Before activation, this covering element is kept in the withdrawn position by immobilization means. This injection device also comprises means of retaining the covering element. These retention means make it possible to prevent the deployment of the covering element after activation of the immobilization means. The retention means are released by simply relaxing the distal pressure applied to the piston rod to allow the deployment of the covering element. This injection device nevertheless does not make it possible to remove the risk of reabsorption when the user relaxes the pressure on the piston rod before withdrawing the injection needle from the injection site.

There is therefore the need for an injection device that prevents the return of the piston after injection and that is furnished with needle protection means that can be activated automatically but only when the end-user so decides, making it possible, after activation of the protection means, to allow the injection of the end of the dose and that is easy to manufacture.

The object of the invention is therefore to provide an injection device, particularly a syringe, furnished with needle protection means activated automatically at the end of injection but preventing the return of the piston after injection.

Another object of the invention is to provide such an injection device whose automatic protection means cannot be activated inadvertently, thus providing perfect safety against the risks of accidental pricks.

Another object of the invention is to propose such an injection device with automatic protection means making it possible to inject the end of the dose and capable of being easily manufactured industrially.

The present invention relates to an injection device comprising at least:
  a substantially tubular body designed to receive a product to be injected, the said body being furnished at its distal end with an injection needle, the said body receiving a piston rod and a piston capable of moving in the said body between a storage position and an end-of-injection position and of pushing the said product through the said injection needle,
  means of protecting the injection needle comprising at least:
    an element for covering the said injection needle, the said covering element being movable relative to the said body between at least an initial position, in which the injection needle is uncovered, and a final position, in which the said injection needle is at least partially covered,
    biasing means arranged to aim at moving the said covering element between said initial and final positions,
    immobilization means arranged to aim at holding the said covering element in at least one of said initial and final positions,
  the said injection device being characterized in that:
    the said piston rod comprises at least a first portion and a second portion operatively coupled together and selectively movable together in the distal direction, at least one of said first portion and said second portion being movable in the proximal direction separate from said other one of said first portion and said second portion.

Document U.S. Pat. No. 4,915,692 describes an injection device comprising a piston rod comprising two portions, a rod portion and a portion for connection to the piston. However, the connection portion is not allowed to move in longitudinal translation relative to the rod portion between two predefined positions.

The injection device according to the invention makes it possible to prevent the piston from moving backwards again when the needle protection means are triggered at the end of injection, particularly when this triggering is performed while the needle is still in the injection site.

Specifically, because a portion of the piston rod is able to move proximally separately from the other portion, for example at least over a predetermined distance, the proximal deployment of the biasing means on the piston rod, when the covering element is pressing against the injection site, is absorbed by the proximal movement of that portion, this absorption allowing the other portion to be unaffected and remain immobile relative to the body of the injection device. Thus, the injection device according to the invention makes it possible to prevent the reabsorption of a portion of the medicine already injected, when the needle covering element, that is to say the needle protection means, moves into place automatically.

The injection device according to the invention therefore makes it possible to limit the risks due to a faulty, in particular diminished, administration of the dose of prescribed medicine while offering safe use.

In an embodiment of the invention, said biasing means are arranged to aim at moving said one of said first portion and said second portion in the proximal direction separate from said other one of said first portion and said second portion.

In an embodiment of the invention, the injection device comprises at least one pressing stop and one complementary pressing stop, one being provided on the said first portion, the other on the said second portion, the said pressing and complementary pressing stops being arranged so as to be operatively coupled together when said piston rod is moved between said storage position and said end-of-injection position.

In an embodiment of the invention, said pressing stop and said complementary pressing stop are arranged so as not to be operatively coupled together when said at least one of said first portion and said second portion is caused to move in the proximal direction.

In an embodiment of the invention, the injection device comprises at least one retraction stop and one complementary retraction stop, one being provided on the said first portion, the other on the said second portion, the said retraction and complementary retraction stops being respectively offset proximally relative to the said pressing stop and complementary pressing stop and being arranged so as to be operatively coupled together when said at least one of said first portion and said second portion is caused to move in the proximal direction.

In an embodiment of the invention, the injection device comprises a sheath at least partly receiving the said body, the said biasing means, and the said immobilization means, said sheath being coupled with the said covering element.

In an embodiment of the invention, the covering element is able to adopt an intermediate position, distally spaced apart from said initial position, and in which said injection needle is uncovered In an embodiment of the invention, said immobilizing means comprise first holding means arranged for holding said covering element in said initial position, intermediate holding means arranged for holding said covering element in said intermediate position, and final holding means arranged for holding said covering element in said final position.

In an embodiment of the invention, said first holding means is arranged so as to be released by one of said first portion and said second portion when said piston rod and piston are moved toward said end-of-injection position.

In an embodiment of the invention, said intermediate holding means is arranged so as to be released when said one of said first portion and said second portion is caused to move in the proximal direction.

In an embodiment of the invention, said first holding means are placed between the said sheath and the said covering element, and said injection device comprises automatic activation means arranged to automatically activate the said intermediate holding means during the distal movement of the said piston rod and piston from the said storage position to the said end-of-injection position.

In an embodiment of the invention, the injection device also comprises means of automatically releasing the said first holding means.

In an embodiment of the invention, the injection device comprises at least one intermediate element placed between the said second portion and the said covering element, the said intermediate element comprising at least a portion of the said automatic means of releasing the said first holding means and/or the said automatic means of activating the said intermediate holding means, the said intermediate element being capable of movement with respect to said sheath and of interacting with the said second portion when the said piston rod and piston moves distally from the said storage position to the said end-of-injection position.

In an embodiment of the invention, said intermediate element also comprises at least a portion of automatic means of deactivating the said intermediate holding means, the said intermediate element being capable of movement with respect to said sheath and of interacting with the said second portion when distal pressure exerted on the said second portion of the said piston rod is relaxed.

In an embodiment of the invention, said first holding means comprise at least one elastically flexible immobilization lug defining an immobilization hook pressing on at least one immobilization surface, at least one of the said immobilization lug/immobilization surface being provided on the said covering element, the other being provided on the said sheath, the said immobilization lug being designed to be deflected by the said second portion or by the said intermediate element in order to be disengaged from the said immobilization surface.

In an embodiment of the invention, said intermediate holding means comprise at least one elastically flexible retention lug defining a retention hook pressing on at least one retention surface, one of the said retention lug/retention surface being provided on the said covering element or the said sheath, the other being provided respectively on the said sheath or on the said covering element, the said retention lug being designed to be deflected by the said second portion or by the said intermediate element in order to be disengaged from the said retention surface.

Preferably, said immobilization lug and the said immobilization hook are substantially distally offset relative respectively to the said retention lug, and to the said retention hook so as to allow a preactivation of the said intermediate holding means prior to the release of the said first holding means when the said piston moves distally from the said storage position to the said end-of-injection position.

Thus, the release of the said first holding means automatically causes the activation of the said intermediate holding means: the latter thus keep the covering element in the intermediate position while the user continues to exert a distal pressure on the piston rod. After release of the first holding means, the deployment of the covering element is therefore subject to the decision of the end-user to relax the pressure on the piston rod.

In an embodiment of the invention, said intermediate element comprises at least a ring having at least a leg extending in the proximal direction, at least a guide lug extending in the distal direction and defining a longitudinal recess, the said ring also being provided with at least a protrusion extending in the distal direction and defining at least an external ramp.

In an embodiment of the invention, said sheath comprises at least one protrusion defining at least one of the said immobilization surface/retention surface.

In an embodiment of the invention:
the said covering element comprises at least the said retention lug extending in the proximal direction,
the said sheath comprises at least one protrusion defining at least the said retention surface,
the said second portion comprises at least one distal skirt capable of pressing on, and distally pushing, the said leg under the action of a distal pressure exerted on the said second portion between the storage position and the end-of-injection position, causing the distal movement of the said ring, the said guide lug causing the said retention lug to flex into the said recess under the action of this movement, the said retention hook then pressing on the said retention surface.

In an embodiment of the invention:
the said covering element comprises at least the said immobilization lug extending in the proximal direction,
the said sheath comprises a protrusion defining at least the said immobilization surface,
the said second portion comprises at least one distal skirt capable of pressing on, and pushing distally, the said leg under the action of a distal pressure exerted on the said second portion between the storage position and the end-of-injection position, causing the distal movement of the said ring, the said external ramp, under the action of this movement, causing the said immobilization lug to flex, the said immobilization hook then pressing on the said immobilization surface.

In an embodiment of the invention, said ring is arranged, when the distal pressure exerted on the said second portion is relaxed, in order to move proximally and cause the said retention lug to be released from the said recess, the said retention lug then deflecting and allowing the distal movement of the said covering element towards its final position.

In an embodiment of the invention, said pressing stop, said complementary pressing stop, said retraction stop, and said complementary retraction stop are arranged so that said second portion is spaced apart from said first portion by a distance D of less than 10 mm when said second portion is moved in the proximal direction separate from said first portion.

Preferably, said distance D is less than or equal to 5 mm and preferably less than or equal to 3 mm.

In an embodiment of the invention, said first and second portions are acted upon longitudinally in opposite directions by at least one deformable element, so that in the said storage position, said pressing stop and complementary pressing stop are operatively coupled together.

In an embodiment of the invention, the said biasing means comprise at least a spring.

In embodiments of the device of the invention, said at least one of said first portion and said second portion being movable in the proximal direction separate from each other between a pressing position and a retraction position of the piston rod, said first and second portions are acted upon longitudinally in opposite directions by at least one or more elastically deformable elements so that they aim at remaining in one of said pressing position or retraction position, irrespective of the position of the injection device in space, when the injection device is in the storage position.

In one embodiment of the invention, said first portion and said second portion are maintained in the pressing position by said at least one or more elastically deformable elements; when said injection device is in the storage position.

In another embodiment of the invention, said first portion and said second portion are maintained in the retraction position by said at least one or more elastically deformable elements; when said injection device is in the storage position.

Such embodiments of the invention, in which the first portion and the second portion are maintained in one of the pressing or retraction positions of the piston rod when the injection device is in the storage position is very reassuring for the user, who can then handle the injection device without feeling parts moving within the device.

The present invention will now be described in greater detail with the aid of the following description and the appended drawings in which.

Figure 1:
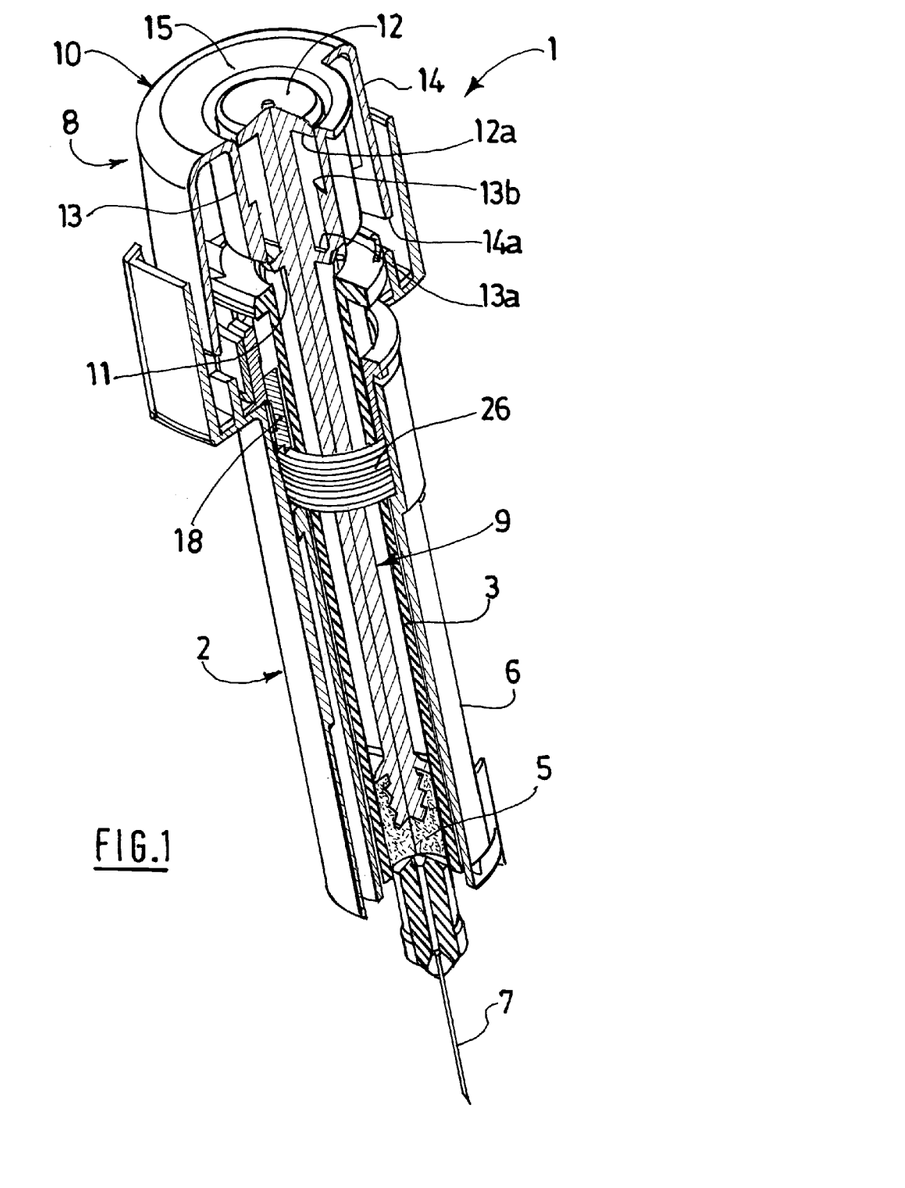
FIG. 1 represents a view, in perspective in partial section, of an injection device according to the invention.

FIG. 1 shows an injection device 1 according to the invention in the end-of-injection position. This injection device 1 comprises a sheath 2 capable of receiving a tubular body 3 of an injection apparatus, for example of a syringe as represented or of any other receptacle such as a phial, this injection apparatus comprising a product to be injected. The body 3 is furnished at its distal end with an injection needle 7. This injection needle 7 may be bonded to the distal end or fitted for example by means of a Luer-type connector. The body 3 houses a piston 5 that is attached to the distal end of a piston rod 8. The piston 5 may be attached to the piston rod 8 by any means, for example screwing, bonding or other means. The piston rod 8 and the piston 5 are capable of moving in the body 3 between a storage position and an end-of-injection position. In particular, under the effect of a distal pressure exerted on the piston rod 8, the piston 5 pushes the product to be injected towards the distal end of the body 3 and therefore through the injection needle 7.

Figures 8A, 8B, 9:
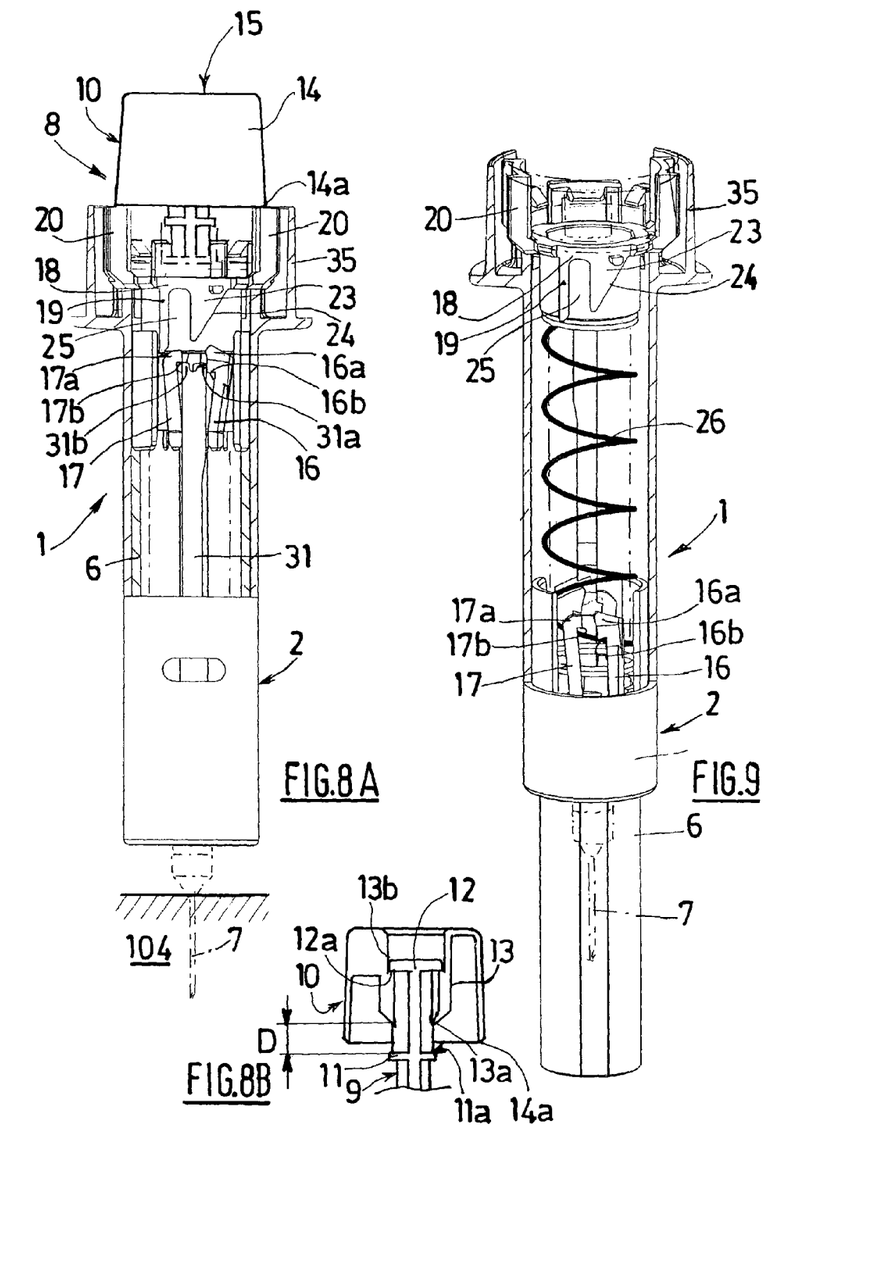
FIG. 8A is a side view of the injection device of FIG. 1 during deactivation of the intermediate holding means.
FIG. 8B is a view in partial section of the piston rod of the injection device of FIG. 8A.
FIG. 9 is a side view of the injection device of FIG. 4 with the protection means protecting the injection needle.

The injection device 1 of the invention of FIG. 1 also comprises means of protecting the injection needle 7 provided with a covering element, that is a sleeve 6 in the example shown. This sleeve 6 is capable of moving relative to the body 3 so as to be able to adopt at least an initial position, for example a withdrawn position, as shown in FIG. 1, in which the injection needle 7 is uncovered, or else a final position, for example an extended position, as shown in FIG. 9, in which the sleeve 6 entirely covers the injection needle 7, thus preventing the risks of accidental pricking after use. As will be seen hereinafter, the travel of the sleeve 6 from its withdrawn position to its extended position is, in this example, allowed by the user relaxing the distal pressure exerted on the piston rod 8.

In particular, the movement of the sleeve 6 from its withdrawn position to its extended position is due to the return to a relaxed state of previously compressed biasing means, for example elastic means. These elastic means are, in the example shown, in the form of a spring 26.

Figure 2:
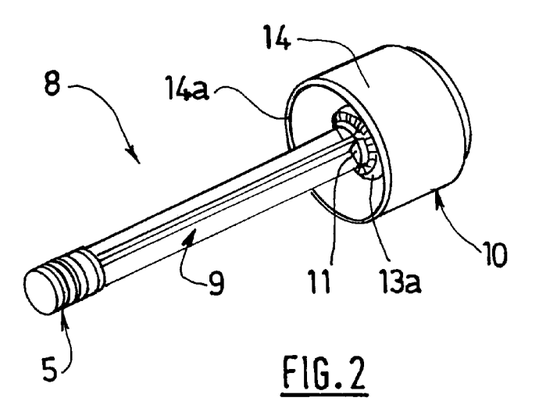
FIG. 2 is a view in perspective of the piston rod of the injection device of FIG. 1, FIGS. 3A and 3B are cutaway views in perspective of the piston rod of the injection device of FIG. 1, when the pressing stop and the complementary pressing stop are operatively coupled one to the other, respectively when the retraction stop and the complementary retraction stop are operatively coupled one to the other.
Figures 3A, 3B:
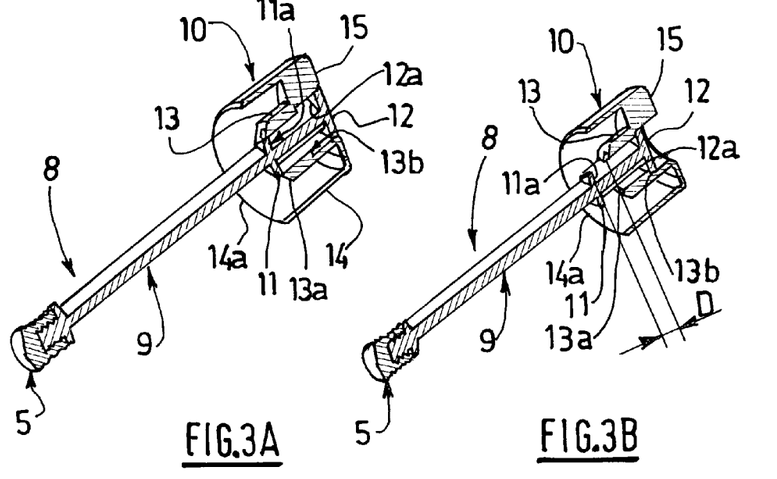

As appears more clearly in FIGS. 2 to 3B, the piston rod 8 comprises a first portion 9 in the form of a rod to the distal end of which is attached a piston 5, and a second portion 10 placed at the proximal portion of the piston rod 8 and forming a head thereto. As explained hereinafter, the said second portion 10 and the said first portion 9 are movable in longitudinal translation relative to one another between at least two predefined positions called respectively the pressing position and the retraction position.

In embodiments shown on FIGS. 10A to 14C and further described hereinafter, the first portion and the second portion are acted upon longitudinally in opposite directions by at least one or more elastically deformable elements so that they aim at remaining either in the pressing position or in the retraction position, irrespective of the position of the injection device in space, particularly when the device is in the storage position.

The first portion 9 and the second portion 10 are furnished with radial stops limiting the translation of the second portion 10 relative to the first portion 9. For this purpose, the first portion 9 comprises, at its proximal end, two transverse walls 11, 12 in the form of a proximal disc 12 and of a distal disc 11. The proximal face of the distal disc 11 forms a pressing stop 11a defining a pressing position of the second portion 10 and the distal face of the proximal disc 12 forms a retraction stop 12a defining a retraction position of the second portion 10.

The second portion 10 of the piston rod 8 comprises two concentric cylindrical skirts, an inner skirt 13, and an outer skirt 14, connected together by a transverse wall 15 forming a pressing surface allowing the user to exert a distal pressure on the piston rod 8. The end of the inner skirt 13 forms a complementary pressing stop 13a designed to receive the pressure of the pressing stop 11a in the pressing position. In addition, the inner skirt 13 is furnished on its inner wall with a crank defining a complementary retraction stop 13b designed to receive the pressure of the retraction stop 12a in the retraction position. As appears in FIG. 3A, under the effect of a distal pressure exerted on the pressing surface 15 of the piston rod 8 by a user, the said second portion 10 is kept in a pressing position by keeping the complementary pressing stop 13a of the inner skirt 13 of the said second portion 10 in contact on the said pressing stop 11a made on the said first portion 9. Because the first and second portions 9, 10 are thus abutting one another, the operation of the injection device 1 according to the invention in no way differs from the injection devices of the prior art, at least as far as the start of the proper injection phase is concerned. The user therefore has no need to modify his mode of operation.

In particular, as will appear further on, the first portion 9 and the second portion 10 are operatively coupled together: thus, as explained hereinabove, they are selectively movable together in the distal direction but at least one of them is movable in the proximal direction separate or independent from the other. In the example shown, the second portion 10 is able to move in the proximal direction independently from the first portion 9, for example at least on a predetermined distance. As shown on FIG. 3B, the pressing stop 11a, the complementary pressing stop 13a, the retraction stop 12a, and the complementary retraction stop 13b are arranged so that the second portion 10 is spaced apart from the first portion 9 by a distance D of less than 10 mm when the second portion 10 is moved in the proximal direction separate from the first portion 9. The distance D is preferably less than or equal to 5 mm and more preferably less than or equal to 3 mm.

More particularly, the pressing stop 11a and the complementary pressing stop 13a are operatively coupled one to the other. Nevertheless, when the second portion 10 is caused to move in the proximal direction, the pressing stop 11a and the complementary pressing stop 13a are not operatively coupled one to the other (cf. FIG. 8B). But in this retraction position, the retraction stop 12a and the complementary retraction stop 13b are operatively coupled one to the other.

In FIG. 3B, the second portion 10 of the piston rod 8 is in its retraction position. This retraction position may be reached, as will be detailed hereinafter, under the action of elastic means (not shown in FIG. 3B) exerting a proximal pressure on the said second portion 10 of the piston rod 8, in particular on the distal end 14a of its outer skirt 14, and keeping the complementary retraction stop 13b of the inner skirt 13 pressing against the retraction stop 12a of the disc 12 of the first portion 9 of the piston rod 8.

Figure 4:
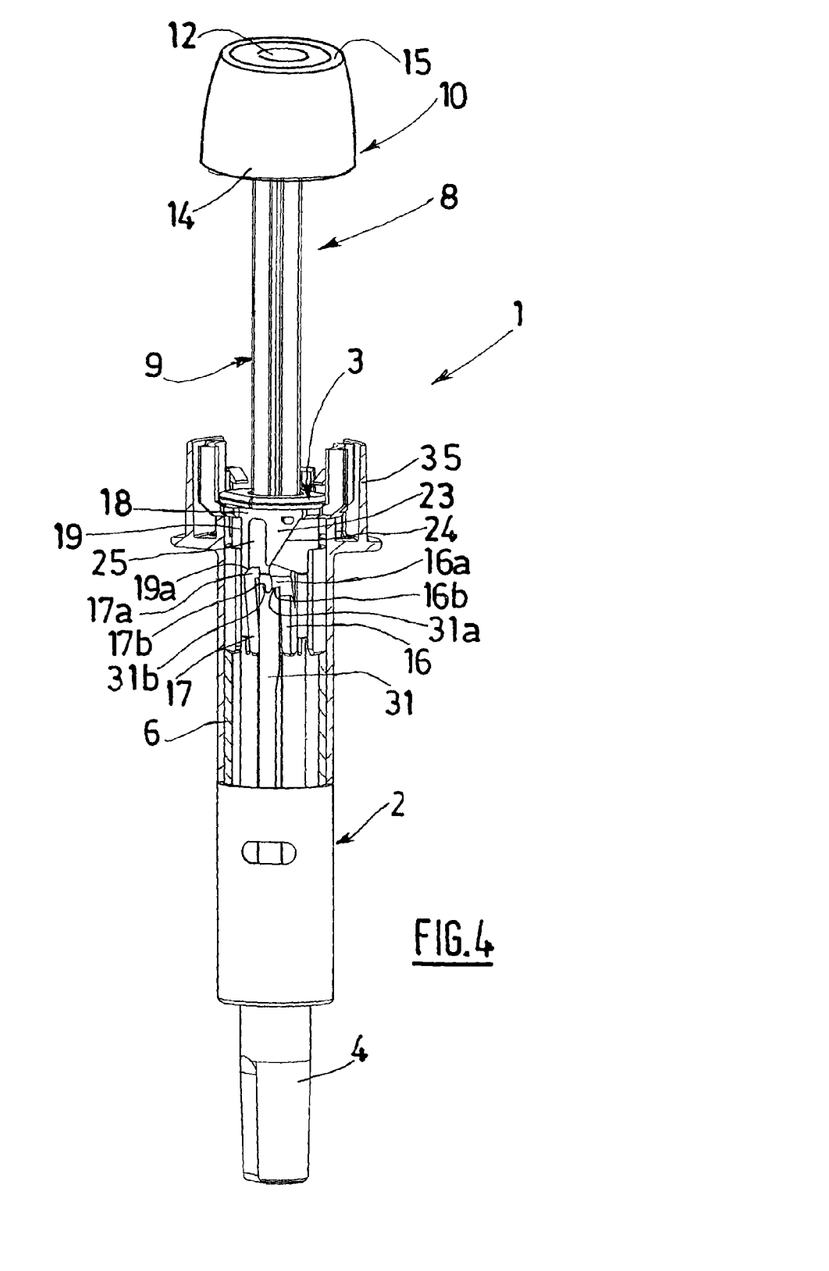
FIG. 4 is a side view of the injection device of FIG. 1, in start-of-injection position.

In FIG. 4, the injection device 1 according to the invention is shown in initial position before injection and the injection needle 7 is still covered by a cap 4.

Figure 5:
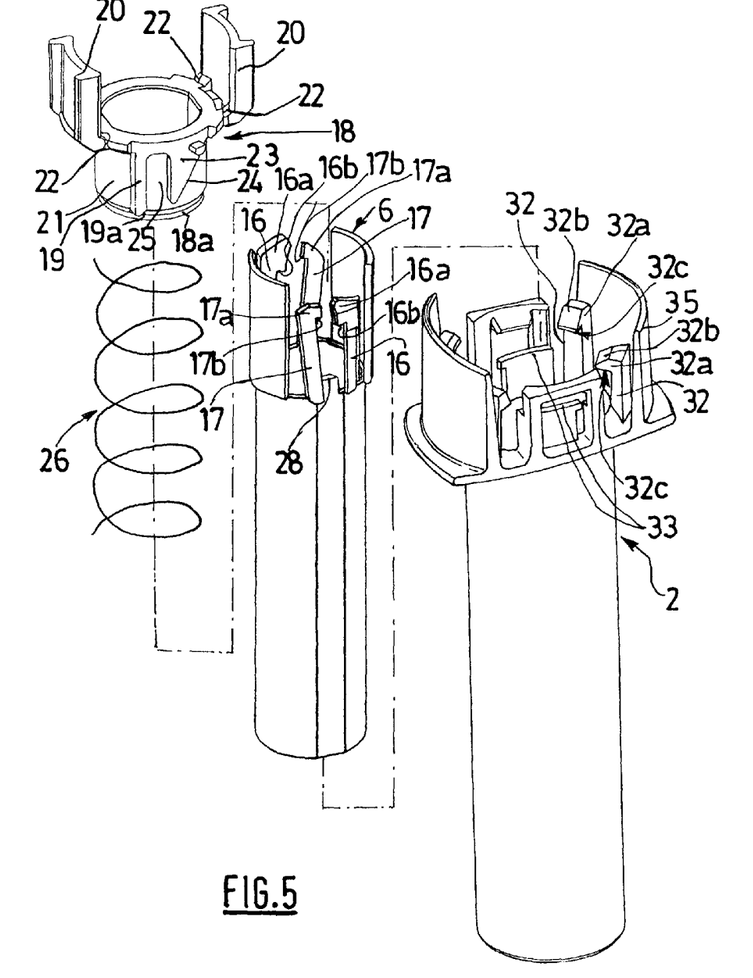
FIG. 5 is an exploded view in perspective showing the protection means and the immobilization means of the injection device of FIG. 1.
Figures 6A, 6B, 7:
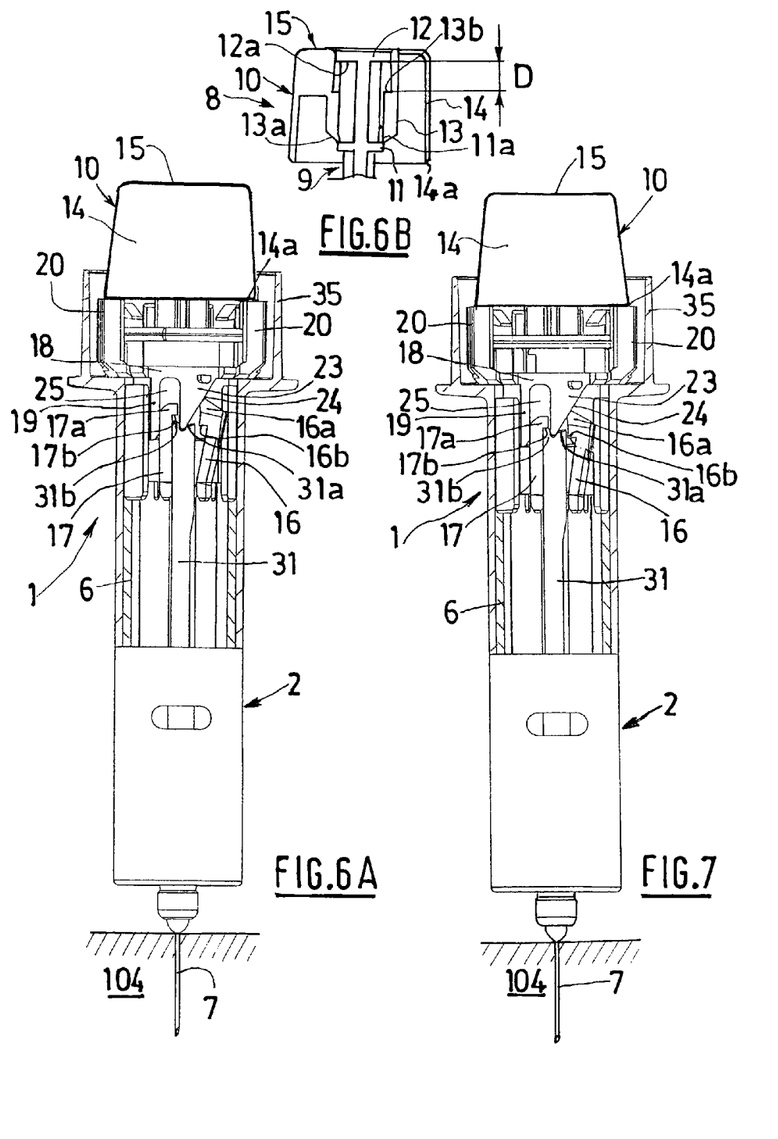
FIG. 6A is a side view of the injection device of FIG. 1, during deactivation of the first holding means.
FIG. 6B is a view in partial section of the piston rod of the device of FIG. 6A.
FIG. 7 is a side view of the injection device of FIG. 1 showing the first holding means deactivated and the intermediate holding means activated.

As shown in FIGS. 4 and 5 and as will appear more clearly in FIGS. 6A and 7, the injection device 1 comprises first holding means for immobilizing the sleeve 6 in its withdrawn position during at least the beginning of a phase, called the injection phase, and this is so irrespective of whether the pressure exerted on the piston rod 8 is increased or relaxed. These first holding means comprise two longitudinal protrusions 31 provided on the inner surface of the wall of the sheath 2 and two elastically flexible immobilization lugs 16 extending axially in the proximal direction from the proximal end of the sleeve 6. Preferably, the protrusions 31 are diametrically opposed. Each protrusion 31 comprises, at its proximal end, an immobilization surface 31a provided in relief and each immobilization lug 16 is furnished at its proximal end with an immobilization hook 16a whose distal face 16b is capable of resting on the immobilization surface 31a of the protrusion 31 placed opposite. As will be explained hereinafter, these first holding means for immobilizing the sleeve 6 are capable of being released automatically during the injection, the said sleeve 6 being then kept in the intermediate position, in which the injection needle 7 is uncovered, by intermediate holding means described hereinafter.

As shown in FIGS. 4 and 5 and as will appear more clearly in FIGS. 6A and 7, the injection device 1 also comprises intermediate holding means for retaining the sleeve 6 in its intermediate position during at least the end of the injection phase, after automatic release of the first holding means. These intermediate holding means comprise the two longitudinal protrusions 31 previously described. Accordingly, each longitudinal protrusion 31 comprises at its proximal end a retention surface 31b provided in relief. The intermediate holding means also comprise two elastically flexible retention lugs 17, extending axially in the proximal direction from the proximal end of the sleeve 6. Each retention lug 17 is furnished at its proximal end with a retention hook 17a whose distal face 17b is capable of pressing on the retention surface 31b of the protrusion 31 placed opposite.

In the example described, each protrusion 31 comprises an immobilization surface 31a and a retention surface 31b placed in the extension of one another. In other embodiments not shown, the injection device may comprise a protrusion provided with a retention surface and an immobilization surface that are at a distance. Likewise, the injection device may comprise one or more retention protrusions and one or more distinct immobilization protrusions, each retention protrusion comprising only one or more retention surfaces, each immobilization protrusion comprising only one or more immobilization surfaces.

As will be explained hereinafter, in the example described:
at the start of injection, the intermediate holding means for retaining the sleeve 6 are in an inactive position in which the retention lug 17 is at rest, flexed laterally, the retention hook 17a therefore not being in the alignment of the protrusion 31: the distal face 17b of the hook 17a is therefore not engaged with the retention surface 31b of the protrusion 31 and does not retain the distal translation of the sleeve 6, this translation then still being prevented by the first holding means,
during injection, more precisely towards the end of the injection, the intermediate holding means move to a preactivation position: more precisely, the retention lug 17 is straightened under stress so that the retention hook 17a comes in the alignment of the protrusion 31 without however pressing on this protrusion,
then, the first holding means are released, the sleeve 6 moves distally over a short distance until the distal face 17b of the retention hook 17a comes to press on the retention surface 31b of the protrusion 31: the intermediate holding means are then in the active position and prevent the distal translation of the sleeve 6, the sleeve 6 being then in the intermediate position,
at the end of injection, the intermediate holding means are deactivated by relaxing the pressure applied on the second portion 10 which, acted upon by the spring 26, moves proximally, releasing, via an intermediate element described hereinafter, the retention lug 17 which flexes to its rest state, then disengaging the retention hook 17a from the protrusion 31 and allowing at the end of injection the movement of the sleeve 6 from its intermediate position to its final position.

In another embodiment not shown, the intermediate holding means for retaining the sleeve are, at the outset, in an active position. The retention lug is then engaged with the protrusion and the injection device comprises active means of releasing this retention lug at the end of injection. In such an embodiment, the sleeve directly moves from its initial position to its final position without adopting an intermediate position.

To improve the grip of the immobilization hook 16a and retention hook 17a respectively on the immobilization surface 31a and retention surface 31b of the protrusion 31, the distal faces 16b and 17b and the immobilization face 31a and retention face 31b may be provided inclined.

As appears in FIGS. 4 and 5, the injection device 1 also comprises an intermediate element, namely a ring 18 situated in the extreme proximal portion 35 of the sheath 2. The extreme proximal portion 35 of the sheath 2 comprises coupling lugs 32, each coupling lug 32 comprising a radial crank 32a whose distal face 32c is designed to retain the proximal face of the ring 18 in the proximal direction, the said radial crank 32a comprising an internal ramp 32b whose function will be explained hereinafter. The ring 18 is capable of moving relative to the sheath 2, inside the extreme proximal portion 35 of this sheath 2, between the distal faces 32c of the coupling lugs 32 and of the rims 33. The ring 18 comprises means of interaction with the second portion 10 of the piston rod 8 of the injection device 1. In the example shown, these interaction means are presented in the form of two diametrically opposed legs 20 extending in the proximal direction, slightly offset in the radial direction relative to the body 21 of the ring 18 and connected at the proximal end of the ring 18 by radial bridges 22.

As will appear more clearly in FIGS. 6A to 9, the ring 18 also comprises means of activating the intermediate holding means in the form, in the example shown, of the guide lugs 19 extending distally and placed substantially symmetrically on the ring 18. Each guide lug 19 defines a longitudinal recess 25 designed to receive a retention lug 17 in active position. Each guide lug 19 is provided at its distal end with an activation ramp 19a designed to facilitate the flexing and the insertion of the retention lug 17 into the longitudinal recess 25 when the intermediate holding means travel from their inactive to active position. The ring 18 also comprises means of releasing the first holding means, in the form, in the example shown, of a surface 23 protruding radially from the body 21 of the ring 18, this surface 23 being capable of interacting with the immobilization lugs 16 in order to flex them circumferentially. In the example shown, this surface 23 has an external ramp 24 opposite each immobilization lug 16.

The proximal end of the spring 26 presses on the distal end 18a of the ring 18 (see FIG. 5) and its distal end presses on an annular rim 28 made on the inner surface of the sleeve 6 at its proximal end.

To facilitate assembly, the sheath 2 may be provided in two portions fixed together during the assembly, for example by snap fitting, bonding or any other equivalent technique.

In practice, the injection device 1 according to the invention is in the initial position before injection as shown in FIG. 4. In this position:
the second portion 10 of the piston rod 8 is in the pressing position (see FIG. 3A),
the immobilization lugs 16 are engaged with the immobilization surfaces 31a provided in relief,
the spring 26 is in an at least partially compressed state. The system is thus perfectly locked, with no risk of triggering the activation of the sleeve 6.

To proceed with the injection, the user takes hold of the injection device 1 as shown in FIG. 4, removes the cap 4, applies the injection device 1 to the injection site 104 (see FIG. 6A), inserts the injection needle 7 in the injection site 104 and exerts a distal pressure on the piston rod 8, in particular on the pressing surface 15 of the second portion 10 of the piston rod 8.

During this injection phase, under the effect of the distal pressure exerted by the user on the pressing surface 15, the second portion 10 of the piston rod 8 is kept in its pressing position, as shown in FIG. 6B. In this pressing position, the distal end 13a of the inner skirt 13 of the second portion 10 of the piston rod 8 is abutting, and therefore is operatively coupled with, the pressing stop 11a made on the first portion 9 of the piston rod 8.

Thus, under the effect of the distal pressure exerted by the user on the pressing surface 15 of the second portion 10 of the piston rod 8, the whole piston rod 8, namely the first portion 9 and the second portion 10 together and operatively coupled one to the other, moves in the distal direction and the first portion 9 pushes the piston 5 towards the distal end of the body 3, thus injecting the product.

As is clear from FIG. 4, during the beginning of this injection phase, the first holding means for immobilizing the sleeve 6 in its initial or withdrawn position remain locked. Thus, the sleeve 6 is kept in its withdrawn position by the first holding means irrespective of the value of the distal force exerted by the user on the piston rod 8. In particular, thanks to the first holding means, the sleeve 6 remains in the withdrawn position, even if the user relaxes the distal pressure that he exerts on the piston rod 8 via the pressing surface 15.

Towards the end of the injection, while the injection needle 17 is still inserted into the injection site 104, as shown in FIG. 6A, the second portion 10 of the piston rod 8 of the injection device 1 comes into contact with the ring 18. In particular, the distal end 14a of the outer skirt 14 of the second portion 10 of the piston rod 8 comes into contact with the interaction means, that is to say the legs 20, in the example shown, of the ring 18. By continuing to exert a distal pressure and pushing on the second portion 10 of the piston rod 8, the distal end 14a of the outer skirt 14 of the second portion 10 of the piston rod 8 pushes the legs 20 of the ring 18 and the ring 18 is thus moved in the distal direction. Under the effect of this distal movement of the ring 18, the activation ramps 19a of the guide lugs 19 of the sleeve 6 straighten the retention lugs 17 and force them into the longitudinal recesses 25 so that the hooks 17a are in the trajectory of the protrusions 31 and the intermediate holding means can immobilize the distal translation of the sleeve 6. Successively, the external ramps 24 of the radial protrusion 23 of the intermediate ring 18 deflect the immobilization lugs 16 circumferentially so that they are no longer engaged with the protrusions 31.

Thus, the first holding means for immobilizing the sleeve 6 in its withdrawn position are released and, under the pressure of the spring 26, which tries to return to its relaxed state, the sleeve 6 is moved in the distal direction, over a very short distance, until the distal faces 17a of the retention lugs 17 make contact with the retention surfaces 31b of the protrusions 31 as shown in FIG. 7. The sleeve 6 is then kept in its intermediate position, which is still a withdrawn position of the sleeve 6 in which the injection needle 7 is uncovered, by the intermediate holding means, so long as the user exerts his pressure on the piston rod 8. In this position, the piston (not visible in FIGS. 6A and 7) is almost at the end of travel in the body 3.

To terminate the injection, the user prolongs the distal movement of the piston rod 8 until the piston 5 reaches the bottom of the body 3. The injection of the end of the dose is thus assured.

Throughout the injection phase, the user exerts a distal pressure on the second portion 10 of the said piston rod 8 that is thus kept in its pressing position, as shown in FIG. 6B.

In normal use, once the end of the dose has been assured, the user keeps the pressure on the piston rod 8 and withdraws the injection needle 7 from the injection site 104. It is nevertheless possible that, through lack of training, information or attention, the user relaxes the pressure on the piston rod 8 before withdrawing the injection needle 7 from the injection site 104. With other injection devices comprising automatic protection means activated by the movement of the piston rod, this incorrect use would have the effect of causing a reabsorption of the previously injected product, hence an incorrect dose. Specifically, the injection devices of the prior art usually comprise a spring placed between the sleeve and the piston rod which, after activation of the protection means, if the injection needle is still in the injection site and the sleeve is immobilized by the skin of the patient, causes the piston rod to return and hence a reabsorption phenomenon.

The invention makes it possible to remove this problem. Specifically, if, while the injection needle 7 is still inserted in the injection site 104, and the protection means, namely the covering element or sleeve 6 in the example shown, have been activated, the user relaxes the pressure that he was exerting on the piston rod 8, in particular on the second portion 10, the ring 18 is moved in the proximal direction under the effect of the pressure of the spring 26. Accordingly, the surface 23 protruding radially from the body 21 of the ring 18 releases the retention lugs 17 from the longitudinal recesses 25 as shown in FIG. 8A. These retention lugs 17 resume their initial, slightly inclined position relative to the longitudinal axis of the injection device 1 and the distal retention faces 17*b* of the hooks 17*a* are no longer engaged with the retention surfaces 31*b* of the protrusions 31. The proximal movement of the ring 18 at the same time causes, via the legs 20 that push the distal end 14*a* of the outer skirt 14 of the second portion 10 of the piston rod 8 in the proximal direction, the proximal movement of this said second portion 10.

Furthermore, since the injection needle 7 is kept in the injection site 104, the sleeve 6 cannot move in the distal direction because it is immediately stopped by the surface of the skin of the patient.

However, due to the ability of the second portion 10 of the piston rod 8 to move in the proximal direction separately from said first portion 9, the first portion 9 of the piston rod 8 remains immobile, at least until the second portion 10 reaches its retraction position.

Thus, the ring 18 continues to move in the proximal direction under the action of the spring 26, and pushes the said second portion 10 of the piston rod 8. The second portion 10 may thus move to a retraction position whose end position is delimited by the retraction stop 12*a* made on the first portion 9, as shown in FIG. 8B.

During this step, the first portion 9 of the piston rod 8 has not moved. Specifically, because of the particular design of this piston rod 8, the energy of deployment of the spring 26 which, with other injection devices would have caused the reabsorption of the injected product, is here totally absorbed by the proximal movement of the second portion 10 of the piston rod 8 independently from the first portion 9, from its pressing position to its retraction position. Consequently, the first portion 9 of the piston rod 8 has remained immobile and the piston 5, which is connected thereto, has not moved either. In particular, it has not been subjected to a return movement. The risk of reabsorption of medicine has thus been prevented.

Preferably, the distance separating the pressing position of the second portion 10 of the piston rod 8 from its retraction position, that is to say the distance separating the first portion 9 from the second portion 10 when the latter has moved in the proximal direction, is sufficient to absorb the beginning of deployment of the spring 26. For example, this distance, symbolized by the letter D in FIGS. 6B and 8B, may be from 1 to 10 mm. Preferably, this distance is less than or equal to 5 mm, still preferably less than or equal to 3 mm.

The user may then choose to withdraw the injection needle 7 from the patient at that moment only.

Under the effect of the pressure of the spring 26, the sleeve 6 is then moved in the distal direction and comes to cover the injection needle 7 that is shown in dot-and-dash lines in FIG. 9. Then final holding means (not shown), such as legs, provided on the sheath or on the sleeve, capable of engaging recesses provided on the sleeve, respectively on the sheath, immobilize the sleeve in this final position.

With reference to FIGS. 10A to 14C are shown variant embodiments of piston rods suitable for the device of the invention.

In particular, with reference to FIGS. 10A to 11C are shown embodiments of a piston rod in which the first portion and the second portion are acted upon longitudinally in opposite directions by one or more elastically deformable elements so that they aim at remaining in the pressing position, irrespective of the position of the injection device in space, when the injection device is in the storage position.

Figure 10A:
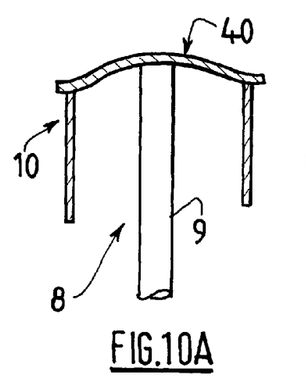
FIGS. 10A to 10C are schematic views of a piston rod of a variant of the device of the invention, respectively before injection, during injection and after the end of injection.
Figure 10B:
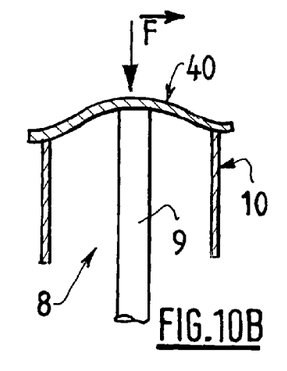

With reference to FIG. 10A is shown schematically a piston rod 8 having a first portion 9 and a second portion 10. The proximal part of the second portion 10 is made of an elastically deformable cover 40. This elastically deformable cover may be made out of a material such as plastic, metal, etc. The elastically deformable cover 40 is such that it acts upon said first and second portions (9,10) so that they are maintained in the pressing position of the piston rod 8, as shown on FIG. 10A, when the injection device (not shown) is in its storage position, before use. On FIG. 10B is shown the position of the piston rod 8 during injection. The distal pressure exerted by the user (shown by arrow F on FIG. 10B) allows the injection to be completed but is not important enough to deform the cover 40 at that stage. At the end of injection, when the user releases the distal pressure he exerted on the piston rod 8, the second portion 10 is pushed in the proximal direction (represented by arrows P on FIG. 10C) by the ring 18 and the spring 26 as explained before for FIGS. 6-8. The force exerted by the spring 26 on the second portion 10 via the ring 18 is sufficient to deform the elastically deformable cover 40. As shown on FIG. 10C, the deformation of the elastically deformable cover 40 allows the second portion 10 to move in the proximal direction with respect to the first portion 9 and the piston rod 8 is now in its retraction position.

Figure 10C:
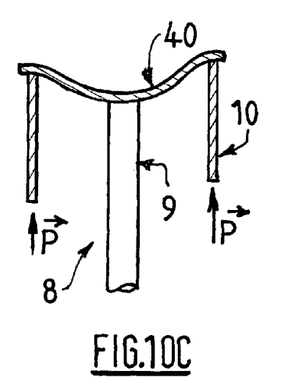
Figure 11A:
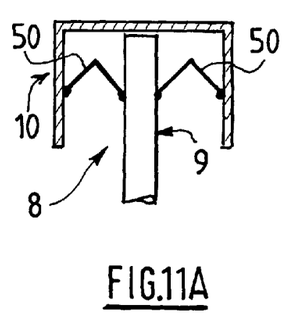
FIGS. 11A to 11C are schematic views of a piston rod of another variant of the device of the invention, respectively before injection, during injection and after the end of injection.
Figures 11B, 12B:
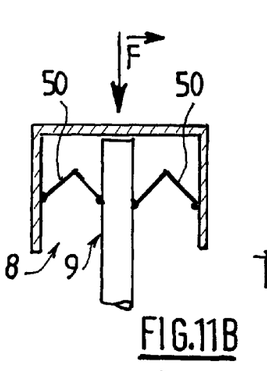
FIGS. 12A to 12C are schematic views of a piston rod of a variant of the device of the invention, respectively before injection, during injection and after the end of injection.
Figure 11C:
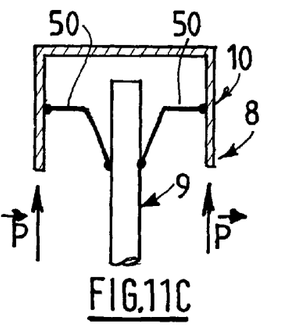

FIGS. 11A to 11C show a variant of the embodiment of FIGS. 10A to 10C in which the elastically deformable cover is replaced by at least two elastically deformable strings 50 located between the first portion 9 and the second portion 10. The operation of the piston rod 8 of FIGS. 11A to 11C is identical to that of FIGS. 10A to 10C. On FIG. 11A, the injection device (not shown) is in its storage position, before use and the piston rod 8 is in its pressing position thanks to the elastically deformable strings 50 acting upon said first and second portions (9, 10) On FIG. 11B, the piston rod 8 is still in its pressing position during injection. On FIG. 11C, the force exerted by the spring 26 has deformed the strings 50 and the second portion 10 has moved in the proximal direction with respect to the first portion 9: the piston rod 8 is in its retraction position.

With reference to FIGS. 12A to 14C, are shown embodiments of a piston rod 8 in which the first portion 9 and the second portion 10 are acted upon longitudinally in opposite directions by one elastically deformable element (60, 70, 80) so that they aim at remaining in the retraction position, irrespective of the position of the injection device in space, when the injection device is in the storage position.

Figure 12A:
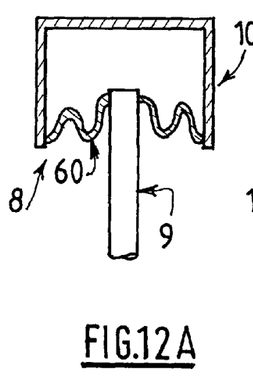

With reference to FIG. 12A is shown schematically a piston rod 8 having a first portion 9 and a second portion 10. An elastically deformable tape 60 is located between the first portion 9 and the second portion 10. This elastically deformable tape may be made out of a material such as plastic, metal, etc. The elastically deformable tape 60 is such that it acts upon said first and second portions (9,10) so that they are maintained in the retraction position of the piston rod 8, as shown on FIG. 12A, when the injection device (not shown) is in its storage position, before use. On FIG. 12B is shown the position of the piston rod 8 during injection. The distal pressure exerted by the user (shown by arrow F on FIG. 10B) overcomes the resistance to deformation of the tape 60 which deforms as shown on FIG. 12B, allowing the second portion 10 to move distally with respect to the first portion 9. The piston rod 8 is there in its pressing position and the injection is allowed to be completed. At the end of injection, when the user releases the distal pressure he exerted on the piston rod 8, the second portion 10 is pushed in the proximal direction (represented by arrows P on FIG. 12C) by the ring 18 and the spring 26 as explained before for FIGS. 6-8. The force exerted by the spring 26 on the second portion 10 via the ring 18 is sufficient to bring the elastically deformable tape 60 to its initial state of FIG. 12A. As shown on FIG. 12C, the return of the elastically deformable tape 60 to its non deformed state allows the second portion 10 to move in the proximal direction with respect to the first portion 9 and the piston rod 8 is now back in its retraction position.

Figure 12C:
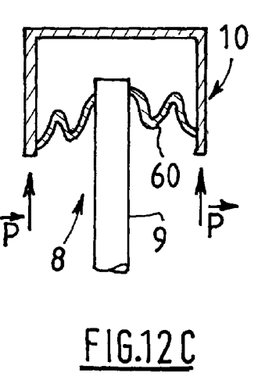
Figure 13A:
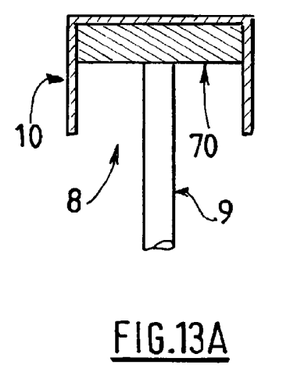
FIGS. 13A to 13C are schematic views of a piston rod of a variant of the device of the invention, respectively before injection, during injection and after the end of injection.
Figure 13B:
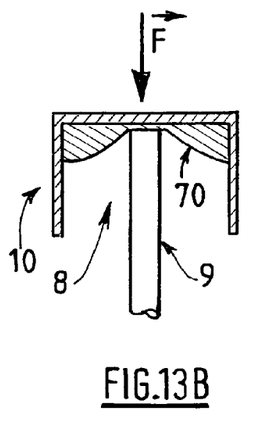
Figure 13C:
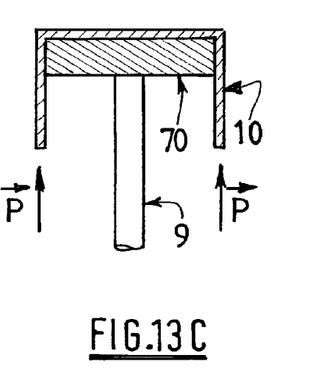

FIGS. 13A to 13C show a variant of the embodiment of FIGS. 12A to 12C in which the elastically deformable tape is replaced by an elastically deformable cushion 70 located between the first portion 9 and the second portion 10. The operation of the piston rod 8 of FIGS. 13A to 13C is identical to that of FIGS. 12A to 12C. On FIG. 13A, the injection device (not shown) is in its storage position, before use and the piston rod 8 is in its retraction position thanks to the elastically deformable cushion 70 acting upon said first and second portions (9, 10) On FIG. 13B, the piston rod 8 is now in its pressing position, the elastically deformable cushion 70 is in its deformed state, the second portion 10 has moved in the distal direction with respect to the first portion 9 and the injection takes place. On FIG. 13C, the force exerted by the spring 26 has caused the return of the elastically deformable cushion 70 to its non deformed state and the second portion 10 has moved in the proximal direction with respect to the first portion 9: the piston rod 8 is in its retraction position.

Figure 14A:
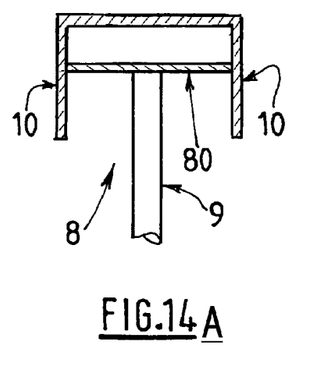
FIGS. 14A to 14C are schematic views of a piston rod of a variant of the device of the invention, respectively before injection, during injection and after the end of injection.
Figure 14B:
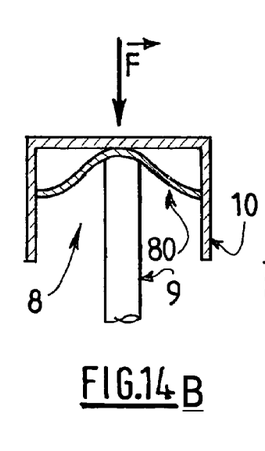
Figure 14C:
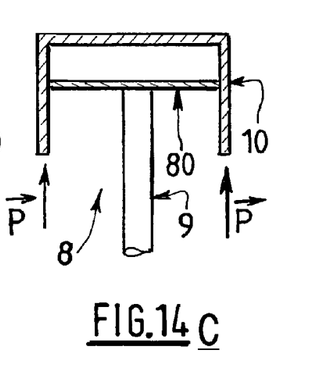

FIGS. 14A to 14C show a variant of the embodiment of FIGS. 12A to 13C in which the elastically deformable tape and cushion are replaced by an elastically deformable strip 80 located between the first portion 9 and the second portion 10. The operation of the piston rod 8 of FIGS. 14A to 14C is identical to that of FIGS. 12A to 13C. On FIG. 14A, the injection device (not shown) is in its storage position, before use and the piston rod 8 is in its retraction position thanks to the elastically deformable strip 80 acting upon said first and second portions (9, 10) On FIG. 14B, the piston rod 8 is now in its pressing position, the elastically deformable strip 80 is in its deformed state, the second portion 10 has moved in the distal direction with respect to the first portion 9 and the injection takes place. On FIG. 14C, the force exerted by the spring 26 has caused the return of the elastically deformable strip 80 to its non deformed state and the second portion 10 has moved in the proximal direction with respect to the first portion 9: the piston rod 8 is in its retraction position.

The advantage of embodiments of the piston rod 8 described in FIGS. 10A to 14C above is that there is no natural possible movement between the first and the second portions when the injection device is in its storage position, irrespective of the position of the injection device in space: this absence of natural movement between two parts of the injection device when the user handles the injection device in whatever position is reassuring for the user.

It is evident from the foregoing that the invention provides determinant enhancements over the similar injection devices of the prior art, by making it possible to prevent the proximal return of the piston at the end of injection while the injection needle is still in the injection site and after the protection means have been activated. The invention makes it possible to benefit from an injection device having automatic protection means while guaranteeing the possibility of injecting the whole dose of product without, for all that, requiring a complex manufacturing method. Specifically, the distance D makes it possible to absorb the dimensional variations.

It goes without saying that the invention is not limited to the embodiment described hereinabove as an example, but that, on the contrary, it embraces all the variant embodiments entering the field of protection defined by the claims appended hereto.

For example, the invention may be applied to other injection devices such as that described in introduction in publication WO 03/068298 A1. In this case, because of the particular design of the piston rod 8 according to the invention, the return energy of the intermediate lugs to their rest position after relaxing the distal pressure exerted on the piston rod 8 is totally absorbed by the movement of the second portion 10 of the piston rod 8 from its pressing position to its retraction position. Consequently, the first portion 9 and the piston 5 remain immobile and the risk of reabsorption of medicine is thus prevented.

The invention also applies to all the injection devices in which the deformable elastically flexible lugs are replaced for example by:
- inelastic and/or pivoting lugs, acted upon laterally by elastic elements,
- posts travelling in grooves and acted upon laterally by elastic elements,
- an additional rotary element, such as for example a collar placed between the intermediate ring and the covering element, this collar being provided with grooves capable of receiving tabs provided on the covering element and forming means of retention or of immobilization, this collar being free to pivot.

The invention claimed is:
1. Injection device comprising:
   a body designed to receive a product to be injected, the body having a distal end with an injection needle, the body receiving a piston rod and a piston capable of moving in the body between a storage position and an end-of-injection position and of pushing the product through the injection needle,
   a cover for the injection needle, the cover being movable relative to the body between an initial position, in which the injection needle is uncovered, and a final position, in which the injection needle is at least partially covered, and
   a spring for moving the cover between said initial and final positions,
   wherein the piston rod comprises a first portion, in the form of a rod having said piston located at a distal end thereof, and a second portion, located radially-outwardly about a proximal portion of said rod, operatively coupled together and selectively movable together in the distal direction, at least one of the first portion and the second portion being movable in the proximal direction separate from the other one of the first portion and the second portion so as to alter the overall length of the piston rod.

2. Injection device according to claim 1, wherein the spring is arranged to aim at moving said one of said first portion and said second portion in the proximal direction separate from said other one of said first portion and said second portion.

3. Injection device according to claim 1, further comprising at least one pressing stop and one complementary pressing stop, one being provided on the first portion, the other on the second portion, the pressing and complementary pressing stops being arranged so as to be operatively coupled together when said piston rod is moved between said storage position and said end-of-injection position.

4. Injection device according to claim 3, wherein said at least one pressing stop and said one complementary pressing stop are arranged so as not to be operatively coupled together when said at least one of said first portion and said second portion is caused to move in the proximal direction.

5. Injection device according to claim 4, further comprising at least one retraction stop and one complementary retraction stop, one being provided on the first portion, the other on the second portion, the retraction and complementary retraction stops being respectively offset proximally relative to the pressing stop and complementary pressing stop and being arranged so as to be operatively coupled together when said at least one of said first portion and said second portion is caused to move in the proximal direction.

6. Injection device according to claim 5, wherein the pressing stop, said complementary pressing stop, said retraction stop, and said complementary retraction stop are arranged so that said second portion is spaced apart from said first portion by a distance D of less than 10 mm when said second portion is moved in the proximal direction separate from said first portion.

7. Injection device (1) according to claim 6, wherein the distance D is less than or equal to 5 mm and preferably less than or equal to 3 mm.

8. Injection device according to claim 3, wherein the first and second portions are acted upon longitudinally in opposite directions by at least one deformable element, so that in the said storage position, said pressing stop and complementary pressing stop are operatively coupled together.

9. Injection device according to claim 1, further comprising a sheath at least partly receiving the said body, and the spring, said sheath being coupled with the cover.

10. Injection device according to claim 1, wherein the cover is able to adopt an intermediate position, distally spaced apart from said initial position, and in which said injection needle is uncovered.

11. Injection device according to claim 10, further comprising first holding means arranged for holding said cover in said initial position, intermediate holding means arranged for holding said cover in said intermediate position, and final holding means arranged for holding said cover in said final position.

12. Injection device according to claim 11, further comprising means of automatically releasing the first holding means.

13. Injection device according to claim 11, wherein said first holding means is arranged so as to be released by one of said first portion and said second portion when said piston rod and piston are moved toward said end-of-injection position.

14. Injection device according to claim 11, wherein said intermediate holding means is arranged so as to be released when said one of said first portion and said second portion is caused to move in the proximal direction.

15. Injection device according to claim 11, further comprising a sheath at least partly receiving the said body, and the spring, said sheath being coupled with the cover, and in that the first holding means are placed between the sheath and the cover, and in that the injection device comprises automatic activation means arranged to automatically activate the intermediate holding means during the distal movement of the said piston rod and piston from the storage position to the end-of-injection position.

16. Injection device according to claim 15, further comprising means of automatically releasing the first holding means.

17. Injection device according to claim 16, further comprising at least one intermediate element placed between the second portion and the cover, the intermediate element comprising at least a portion of the automatic means of releasing the first holding means and/or the automatic means of activating the intermediate holding means, the intermediate element being capable of movement with respect to said sheath and of interacting with the second portion when the piston rod and piston moves distally from the storage position to the end-of-injection position.

18. Injection device according to claim 17, wherein the intermediate element also comprises at least a portion of automatic means of deactivating the intermediate holding means, the intermediate element being capable of movement with respect to said sheath and of interacting with the second portion when distal pressure exerted on the second portion of the piston rod is relaxed.

19. Injection device according to claim 11, further comprising a sheath at least partly receiving the body, and the spring, said sheath being coupled with the cover, and in that the first holding means comprise at least one elastically flexible immobilization lug defining an immobilization hook pressing on at least one immobilization surface, at least one of the immobilization lug/immobilization surface being provided on the cover, the other being provided on the sheath, the immobilization lug being designed to be deflected by the second portion or by the intermediate element in order to be disengaged from the immobilization surface.

20. Injection device according to claim 19, wherein the intermediate holding means comprise at least one elastically flexible retention lug defining a retention hook pressing on at least one retention surface, one of the retention lug/retention surface being provided on the cover or the sheath, the other being provided respectively on the sheath or on the cover, the retention lug being designed to be deflected by the second portion or by the intermediate element in order to be disengaged from the retention surface.

21. Injection device according to claim 20, wherein the immobilization lug and the immobilization hook are substantially distally offset relative respectively to the retention lug, and to the retention hook so as to allow a preactivation of the intermediate holding means prior to the release of the first holding means when the piston moves distally from the storage position to the end-of-injection position.

22. Injection device according to claim 20, wherein the intermediate element comprises at least a ring having at least a leg extending in the proximal direction, at least a guide lug extending in the distal direction and defining a longitudinal recess, the ring also being provided with at least a protrusion extending in the distal direction and defining at least an external ramp.

23. Injection device according to claim 22, wherein:
the cover comprises at least the retention lug extending in the proximal direction,
the sheath comprises at least one protrusion defining at least the retention surface,
the second portion comprises at least one distal skirt capable of pressing on, and distally pushing, the leg under the action of a distal pressure exerted on the second portion between the storage position and the end-of-injection position, causing the distal movement of the ring, the guide lug causing the retention lug to flex into the recess under the action of this movement, the retention hook then pressing on the-retention surface.

24. Injection device according to claim 23, wherein the ring is arranged, when the distal pressure exerted on the second portion is relaxed, in order to move proximally and cause the retention lug to be released from the recess, the retention lug then deflecting and allowing the distal movement of the cover towards its final position.

25. Injection device according to claim 22, wherein:
the cover comprises at least the immobilization lug extending in the proximal direction,
the sheath comprises a protrusion defining at least the immobilization surface,
the second portion comprises at least one distal skirt capable of pressing on, and pushing distally, the leg under the action of a distal pressure exerted on the second portion between the storage position and the end-of-injection position, causing the distal movement of the ring, the external ramp, under the action of this movement, causing the immobilization lug to flex, the immobilization hook then pressing on the-immobilization surface.

26. Injection device according to claim 20, wherein the sheath comprises at least one protrusion defining at least one of the-immobilization surface/retention surface.

27. Injection device according to claim 1, wherein, said at least one of said first portion and said second portion being movable in the proximal direction separate from each other between a pressing position and a retraction position of the piston rod, said first and second portions are acted upon longitudinally in opposite directions by at least one or more elastically deformable elements so that they aim at remaining in one of said pressing position or retraction position, irrespective of the position of the injection device in space, when the injection device is in the storage position.

28. Injection device according to claim 27, wherein said first portion and said second portion are maintained in the pressing position by said at least one or more elastically deformable elements: when said injection device is in the storage position.

29. Injection device according to claim 27, wherein said first portion and said second portion are maintained in the retraction position by said at least one or more elastically deformable elements; when said injection device is in the storage position.

* * * * *